United States Patent [19]

Hamon et al.

[11] Patent Number: 5,439,887

[45] Date of Patent: Aug. 8, 1995

[54] PEPTIDE HAVING ANTIHYPERTENSIVE ACTIVITY FREE OF VASOCONSTRICTOR ACTIVITY

[75] Inventors: Gilles Hamon, Le Raincy; Eve Mahe; Dung Le-Nguyen, both of Montpellier, all of France

[73] Assignee: Roussel-Uclaf, France

[21] Appl. No.: 16,023

[22] Filed: Feb. 10, 1993

[30] Foreign Application Priority Data

Feb. 12, 1992 [FR]  France ................ 92 01557

[51] Int. Cl.⁶ ............... C07K 7/00; C07K 14/00; A61K 38/10; A61K 38/16
[52] U.S. Cl. ...................... 514/13; 530/326
[58] Field of Search ................ 514/13; 530/326

[56] References Cited

FOREIGN PATENT DOCUMENTS 499266A 8/1992 European Pat. Off. .
9202237 2/1992 WIPO .

OTHER PUBLICATIONS

Search Report (Rapport de Recherche) No. 92 01557—Journal of Cardiovascular Pharmacology, vol. 17, Suppl. 7, 1991, Proceedings of the Second International Conference on Endothelin Held at the University of Tsukuba, Japan Dec. 9–Dec. 1990.

*Primary Examiner*—Jill Warden
*Assistant Examiner*—Carol A. Salata
*Attorney, Agent, or Firm*—Bierman and Muserlian

[57] ABSTRACT

A peptide derivative having the formula:

$$X_1-Ser-X_3-X_4-Ser-X_6-Leu-Asp-X_9-Glu-X_{11}-Val-Tyr-X_{14}-Cys-His-X_{17}-Asp-Ile-Ile-X_{21}$$ (SEQ ID NO: 1)

wherein $X_1$ is hydrogen or cysteine residue, $X_3$ is a cysteine or alanine residue, $X_4$ is a residue of asparagine, phenylalanine, leucine, isoleucine, alanine, valine, glycine and their homologues in the D series, $X_6$ is a residue of tryptophan, phenylalanine, leucine, isoleucine, alanine, valine, glycine, serine, lysine, aspartic acid, tyrosine, threonine and their homologues in the D series, $X_9$ and $X_{17}$ are a residue of glutamic acid, aspartic acid, lysine, arginine, tyrosine, leucine and their homologues in the D series, $X_{11}$ is a cysteine or alanine residue, $X_{14}$ is a residue of tyrosine, phenylalanine, leucine, isoleucine, alanine, valine, glycine, serine, lysine, aspartic acid, threonine and their homologues in the D series, $X_{21}$ is hydrogen or a tryptophan or D-tryptophan residue, and the derivatives possessing, where appropriate, one or two disulfide bridges, with the proviso that $X_{21}$ cannot be a tryptophan residue when $X_1$, $X_3$ and $X_{11}$ are a cysteine residue, $X_4$ is an asparagine residue, $X_6$ is a tryptophan residue, $X_9$ is a lysine residue, $X_{14}$ is a phenylalanine residue and $X_{17}$ is a leucine residue having antihypertensive activity free of vasoconstrictor activity.

7 Claims, No Drawings

PEPTIDE HAVING ANTIHYPERTENSIVE ACTIVITY FREE OF VASCOCONSTRICTOR ACTIVITY

STATE OF THE ART

"VIC" (vasoactive intestinal contractor) is known to be a potent vasoconstrictor, cloned and sequenced from the mouse genome and present in the intestine of this species. This peptide, which has recently been isolated, contains 21 amino acids, possesses 2 disulfide bridges and has the formula:

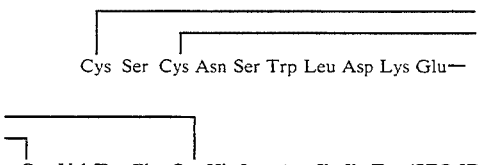

Cys Ser Cys Asn Ser Trp Leu Asp Lys Glu—

—Cys Val Tyr Phe Cys His Leu Asp Ile Ile Trp (SEQ ID NO:2)

(Differential activities of two distinct endothelin family peptides on ileum and coronary artery: ISHIDA, et al., FEBS Letter, (1989), Vol. 247 pp. 337–340). This peptide is designated hereinafter by the name VIC and the nomenclature used is that of the IUPAC-IUB Commission (1984) European J. Biochem, Vol. 183, pp. 9–37.

This peptide, which contains 21 amino acid residues and 2 disulfide bridges, possesses a structure quite similar to that of endothelin. It is capable, after binding to the endothelin receptors, of contracting at very low doses the cells of the smooth muscles (arteries and veins) of various mammalian species (man, dog, cat, pig, guinea pig, rat, rabbit, etc.).

OBJECTS OF THE INVENTION

It is an object of the invention to provide the novel peptides of formula I and a process for their preparation.

It is another object of the invention to provide novel antihypertensive compositions free of vasoconstrictive activity and a method of inducing antihypertensive activity in warm-blooded animals.

These and other objects and advantages of the invention will become obvious from the following detailed description.

THE INVENTION

The novel peptide derivatives of the invention have the formula:

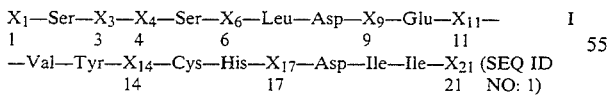

wherein $X_1$ is hydrogen or cysteine residue, $X_3$ is a cysteine or alanine residue, $X_4$ is a residue of asparagine, phenylalanine, leucine, isoleucine, alanine, valine, glycine and their homologues in the D series, $X_6$ is a residue of tryptophan, phenylalanine, leucine, isoleucine, alanine, valine, glycine, serine, lysine, aspartic acid, tyrosine, threonine and their homologues in the D series, $X_9$ and $X_{17}$ are a residue of glutamic acid, aspartic acid, lysine, arginine, tyrosine, leucine and their homologues in the D series, $X_{11}$ is a cysteine or alanine residue, $X_{14}$ is a residue of tyrosine, phenylalanine, leucine, isoleucine, alanine, valine, glycine, serine, lysine, aspartic acid, threonine and their homologues in the D series, $X_{21}$ is hydrogen or a tryptophan or D-tryptophan residue, and the derivatives possessing, where appropriate, one or two disulphide bridges, with the proviso that $X_{21}$ cannot be a tryptophan residue when $X_1$, $X_3$ and $X_{11}$ are a cysteine residue, $X_4$ is an asparagine residue, $X_6$ is a tryptophan residue, $X_9$ is a lysine residue, $X_{14}$ is a phenylalanine residue and $X_{17}$ is a leucine residue.

While attempting to shorten the chain and to replace some of the amino acids of VIC by other amino acids, there has been prepared synthetically the new peptide derivatives of formula I in which the vasoconstrictor activity of VIC has virtually disappeared, and which furthermore possesses the property of blocking and binding to the natural endothelin receptors. The products thus possess an activity which will counteract any action of a subsequent release of endothelin. The products possess, in addition, the advantage of being able to be prepared by total synthesis in large amounts.

When the derivatives of formula I possess disulfide bridges, these bridges can be, for example, at 1-15 and 3-11, or at 1-11 and 3-15.

Among the preferred peptide derivatives of formula I are those wherein $X_4$ is a residue of asparagine, phenylalanine, glycine and their homologues in the D series, $X_6$ is a residue of tryptophan, serine, lysine, aspartic acid, tyrosine, threonine and their homologues in the D series, $X_9$ and $X_{17}$ are a residue of glutamic acid, aspartic acid, lysine, leucine and their homologues in the D series, $X_{14}$ is a residue of tyrosine, phenylalanine and their homologues in the D series, $X_1$, $X_3$, $X_{11}$ and $X_{21}$ have the above meaning, and the derivatives possessing, where appropriate, one or two disulfide bridges as well as the peptide derivatives of formula I wherein:

$X_1$ is a cysteine residue, $X_3$ is a cysteine or alanine residue, $X_4$ is a residue of asparagine, phenylalanine, glycine and their homologues in the D series, $X_6$ is a residue of tryptophan, serine, lysine, aspartic acid, tyrosine, threonine and their homologues in the D series, $X_9$ and $X_{17}$ are a residue of glutamic acid, aspartic acid, lysine, leucine and their homologues in the D series, $X_{11}$ is a cysteine residue, $X_{14}$ is a residue of tyrosine, phenylalanine and their homologues in the D series, $X_{21}$ is a residue of tryptophan and its homologue in the D series, and the derivatives possessing, where appropriate, one or two disulfide bridges.

Among the preferred new peptide derivatives of the invention are the following peptide derivatives:

Cys-Ser-Cys-Phe-Ser-Ser-Leu-Asp-Lys-Glu-Cys-Val-Tyr-Phe-Cys-His-Leu-Asp-Ile-Ile-Trp, (SEQ ID NO: 3)

Cys-Ser-Cys-Gly-Ser-Trp-Leu-Asp-Lys-Glu-Cys-Val-Tyr-Phe-Cys-His-Leu-Asp-Ile-Ile-Trp, (SEQ ID NO: 4)
Cys-Ser-Cys-Asn-Ser-Ser-Leu-Asp-Lys-Glu-Cys-Val-Tyr-Phe-Cys-His-Leu-Asp-Ile-Ile-Trp, (SEQ ID NO: 5)
Cys-Ser-Cys-Phe-Ser-Thr-Leu-Asp-Lys-Glu-Cys-Val-Tyr-Tyr-Cys-His-Leu-Asp-Ile-Ile-Trp, (SEQ ID NO: 6)
Cys-Ser-Cys-Asn-Ser-Tyr-Leu-Asp-Lys-Glu-Cys-Val-Tyr-Phe-Cys-His-Leu-Asp-Ile-Ile-Trp, (SEQ ID NO: 7)
Cys-Ser-Cys-Phe-Ser-Lys-Leu-Asp-Lys-Glu-Cys-Val-Tyr-Phe-Cys-His-Leu-Asp-Ile-Ile-Trp, (SEQ ID NO: 8)

and their derivatives possessing, where appropriate, one or two disulfide bridges and especially the following peptide derivative:

Cys-Ser-Cys-Phe-Ser-Ser-Leu-Asp-Lys-Glu-Cys-Val-Tyr-Phe-Cys-His-Leu-Asp-Ile-Ile-Trp, (SEQ ID NO: 9)

and its derivatives possessing one or two disulfide bridges.

The novel process of the invention for the preparation of the peptide derivatives of formula I comprises performing a solid-phase synthesis by introducing the duly protected amino acids sequentially onto a crosslinked polystyrene type support using a coupling agent, deprotecting the amino acids, releasing the peptide chain thereby formed from the resin, and then, where appropriate, cyclizing the disulfide bridge or bridges to obtain the peptide derivative of formula I.

Under preferred conditions of the process, the crosslinked polystyrene type support is a resin of the "Boc-$X_{21}$-CM" type in which Boc is tert-butyloxycarbonyl, $X_{21}$ has the above meaning and CM is the crosslinked polystyrene support, the coupling agent is benzotriazol-1-yloxytris(dimethylamino)phosphonium hexafluorophosphate or Bop and the release of the peptide chain from the support, as well as the deprotection of the amino acids, is performed with hydrofluoric acid at low temperatures, preferably about 0° C.

The novel antihypertensive compositions of the invention are comprised of an antihypertensively effective amount of at least one peptide derivative of formula I and an inert pharmaceutical carrier. The compositions may be in the form of tablets, dragees, capsules, granules, suppositories, aerosols and injectable solutions or suspensions.

Examples of suitable excipients are talc, gum arabic, lactose, starch, magnesium stearate, cocoa butter, aqueous or non-aqueous vehicles, fats of animal or vegetable origin, paraffin derivatives, glycols, the various wetting, dispersing or emulsifying agents and preservatives.

The compositions of the invention possess very advantageous pharmacological properties; especially noteworthy are an exceptional inhibitory effect against endothelin-induced hypertension and an anti-ischaemic effect, with the vasoconstrictor activity of VIC being abolished. The compositions are useful in the treatment of all vascular spasms, in treatment following cerebral haemorrhage, in the treatment of coronary spasms and of peripheral vascular spasms and also in the treatment of renal insufficiency. These medicinal products may also be used in the treatment of myocardial infarction, in the prevention of restenosis following angioplasty, the treatment of atherosclerosis and of some forms of hypertension and also in the treatment of asthma.

The novel method of the invention for treating hypertension in warm-blooded animals, including humans, comprises administering to warm-blooded animals an antihypertensively effective amount of at least one peptide derivative of formula I. The administration may be oral, rectal or parenteral and the usual daily dose is 0.013 to 4 mg/kg depending upon the condition being treated, the particular peptide derivative and the method of administration.

In the following examples, there are described several preferred embodiments to illustrate the invention. However, it should be understood that the invention is not intended to be limited to the specific embodiments.

EXAMPLE 1

Cys-Ser-Cys-Asn-Ser-Ser-Leu-Asp-Lys-Glu-Cys-Val-Tyr-Phe-Cys-His-Leu-Asp-Ile-Ile-H (SEQ ID NO: 10) (derivative of formula (I) ($X_1$=Cys $X_3$=Cys $X_4$=Asn $X_6$=Ser $X_9$=Lys $X_{11}$=Cys $X_{14}$=Phe $X_{17}$=Leu $X_{21}$=H With 2 disulfide bridges between the cysteines STAGE A: Assembly of the peptide chain A support of the "Boc-Trp-CM-support" type was used, in which Boc was tert-butyloxycarbonyl, Trp is tryptophyl and CM-support is a crosslinked polystyrene support. The support containing 0.6 mmol Trp/g was prepared by the potassium fluoride method by the technique described by Horiki, et al. (1978) Chemistry Lett., pp. 165-168.

All the amino acids were N-protected with tert-butyloxycarbonyl and the protective groups of the side chains were as follows:

p-methylbenzyl for cysteine,
cyclohexyl ester for aspartic acid and glutamic acid,
benzyl for serine,
o-chlorobenzyloxycarbonyl for lysine,
2, 6-dichlorobenzyl for tyrosine,
$N^{im}$-tert-butyloxycarbonyl for histidine,
tryptophan was unprotected.

The coupling reactions were performed using Bop or benzotriazol-1-yloxytris(dimethylamino)phosphonium hexafluorophosphate.

A coupling cycle may be summarised as follows:
Deprotection:
1—Treatment with a solution of trifluoroacetic acid (50%) in dichloromethane containing 3% of ethanedithiol for 1 minute.
2—Draining, then treatment with a 50% solution of trifluoroacetic acid in dichloromethane containing 3% of ethanedithiol for 30 minutes.
3—Draining, then washing with isopropanol containing 5% of ethanedithiol.
4—Washing with dichloromethane twice. Coupling:
1—Addition of Bop and of Boc-amino acid.
2—Addition of diisopropylethylamine (6 equivalents) and then of solvent (dichloromethane or dimethylformamide) with stirring.
3—After negative reaction to ninhydrin, washing twice with dichloromethane.

The checks using ninhydrin were performed according to the method described by Kaiser, et al. (1970) Anal. Biochem., Vol. 24, pp. 595-598.

Before treatment with hydrofluoric acid, the last Boc group was removed with trifluoroacetic acid.

Starting with 2 g of "Boc-Trp-CM-resin" resin, and operating manually, 5.25 g of protected peptide chain-resin complex were thereby obtained and the complex was used directly in the next stage.

STAGE B: Dissociation of the protected peptide chain-resin complex 1.5 g of the protected peptide chain-resin complex were reacted for 60 minutes with 15 ml of hydrofluoric acid at 0° C. in the presence of 1 ml of anisole and 0.5 ml of dimethyl sulfide (0.5 ml). The resin was washed with ether and the crude peptide was extracted with 20% aqueous acetic acid solution. After lyophilisation, 660 mg of the uncyclised crude product were obtained, the product being used directly in the next stage.

STAGE C: Cyclisation and purification 500 mg of the crude peptide of stage B were dissolved in 500 ml of water and the mixture was stirred vigorously. Diisopropylethylamine was added until a pH of 8 was obtained (one drop of mixture was collected every hour and added to one drop of a solution containing dithiobis(2-nitrobenzoic acid) in a molar $K_2HPO_4$ buffer (pH 8) to monitor the oxidation reaction). Throughout the reaction, the pH was maintained at 8 by adding diisopropylethylamine and the reaction was monitored by high performance liquid chromatography (HPLC). After 28 hours, the absence of yellow coloration was noted in the dithiobis(2-nitrobenzoic acid) test.

The product was purified by high performance liquid chromatography (HPLC) on a Whatman M20 $ODS_3$ column and eluted with a water/acetonitrile mixture containing 0.1% of trifluoroacetic acid. The fraction obtained was lyophilised to altar 30 mg of the expected product.

EXAMPLES 2 to 16

Using the procedure of Example 1 but with other amino acids, the other 15 microproteins listed below were prepared.

EXAMPLE 2

Cys-Ser-Cys-Asn-Ser-Trp-Leu-Asp-Lys-Glu-Cys-Val-Tyr-Phe-Cys-His-Leu-Asp-Ile-Ile-H (SEQ ID NO: 11) (derivative of formula (I) ($X_1$=Cys $X_3$=Cys $X_4$=Asn $X_6$=Trp $X_9$=Lys $X_{11}$=Cys $X_{14}$=Phe $X_{17}$=Leu $X_{21}$=H With 2 disulfide bridges between the cysteines 1-15 and 3-11.

EXAMPLE 3

Cys-Ser-Cys-Phe-Ser-Trp-Leu-Asp-Lys-Glu-Cys-Val-Tyr-Phe-Cys-His-Leu-Asp-Ile-Ile-Trp (SEQ ID NO: 12) (derivative of formula (I) ($X_1$=Cys $X_3$=Cys $X_4$=Phe $X_6$=Trp $X_9$=Lys $X_{11}$=Cys $X_{14}$=Phe $X_{17}$=Leu $X_{21}$=Trp With 2 disulfide bridges between the cysteines 1-15 and 3-11.

EXAMPLE 4

Cys-Ser-Cys-Phe-Ser-Ser-Leu-Asp-Lys-Glu-Cys-Val-Tyr-Phe-Cys-His-Leu-Asp-Ile-Ile-Trp (SEQ ID NO: 13) (derivative of formula (I) ($X_1$=Cys $X_3$=Cys $X_4$=Phe $X_6$=Ser $X_9$=Lys $X_{11}$=Cys $X_{14}$=Phe $X_{17}$=Leu $X_{21}$=Trp With 2 disulfide bridges between the cysteines 1-15 and 3-11.

EXAMPLE 5

Cys-Ser-Cys-Asn-Ser-Tyr-Leu-Asp-Lys-Glu-Cys-Val-Tyr-Phe-Cys-His-Leu-Asp-Ile-Ile-Trp (SEQ ID NO: 14) (derivative of formula (I) ($X_1$=Cys $X_3$=Cys $X_4$=Asn $X_6$=Tyr $X_9$=Lys $X_{11}$=Cys $X_{14}$=Phe $X_{17}$=Leu $X_{21}$=Trp With 2 disulfide bridges between the cysteines 1-15 and 3-11.

EXAMPLE 6

Cys-Ser-Cys-Phe-Ser-Ser-Leu-Asp-Glu-Glu-Cys-Val-Tyr-Phe-Cys-His-Leu-Asp-Ile-Ile-Trp (SEQ ID NO: 15) (derivative of formula (I) ($X_1$=Cys $X_3$=Cys $X_4$=Phe $X_6$=Ser $X_9$=Glu $X_{11}$=Cys $X_{14}$=Phe $X_{17}$=Leu $X_{21}$=Trp With 2 disulfide bridges between the cysteines 1-15 and 3-11.

EXAMPLE 7

Cys-Ser-Cys-Gly-Ser-Trp-Leu-Asp-Lys-Glu-Cys-Val-Tyr-Phe-Cys-His-Leu-Asp-Ile-Ile-Trp (SEQ ID NO: 16) (derivative of formula (I) ($X_1$=Cys $X_3$=Cys $X_4$=Gly $X_6$=Trp $X_9$=Lys $X_{11}$=Cys $X_{14}$=Phe $X_{17}$=Leu $X_{21}$=Trp With 2 disulfide bridges between the cysteines 1-15 and 3-11.

EXAMPLE 8

Cys-Ser-Cys-Asn-Ser-Ser-Leu-Asp-Lys-Glu-Cys-Val-Tyr-Phe-Cys-His-Leu-Asp-Ile-Ile-Trp (SEQ ID NO: 17) (derivative of formula (I) ($X_1$=Cys $X_3$=Cys $X_4$=Asn $X_6$=Ser $X_9$=Lys $X_{11}$=Cys $X_{14}$=Phe $X_{17}$=Leu $X_{21}$=Trp With 2 disulfide bridges between the cysteines 1-15 and 3-11.

EXAMPLE 9

Cys-Ser-Cys-Phe-Ser-Asp-Leu-Asp-Lys-Glu-Cys-Val-Tyr-Phe-Cys-His-Leu-Asp-Ile-Ile-Trp (SEQ ID NO: 18) (derivative of formula (I) ($X_1$=Cys $X_3$=Cys $X_4$=Ser $X_6$=Leu $X_9$=Lys $X_{11}$=Cys $X_{14}$=Phe $X_{17}$=Leu $X_{21}$=Trp With 2 disulfide bridges between the cysteines 1-15 and 3-11.

EXAMPLE 10

Cys-Ser-Cys-Phe-Ser-Lys-Leu-Asp-Lys-Glu-Cys-Val-Tyr-Phe-Cys-His-Leu-Asp-Ile-Ile-Trp (SEQ ID NO: 19) (derivative of formula (I) ($X_1$=Cys $X_3$=Cys $X_4$=Phe $X_6$=Lys $X_9$=Lys $X_{11}$=Cys $X_{14}$=Phe $X_{17}$=Leu $X_{21}$=Trp With 2 disulfide bridges between the cysteines 1-15 and 3-11.

EXAMPLE 11

Cys-Ser-Cys-Phe-Ser-Thr-Leu-Asp-Lys-Glu-Cys-Val-Tyr-Tyr-Cys-His-Leu-Asp-Ile-Ile-Trp (SEQ ID NO: 20) (derivative of formula (I) ($X_1$=Cys $X_3$=Cys $X_4$=Phe $X_6$=Thr $X_9$=Lys $X_{11}$=Cys $X_{14}$=Tyr $X_{17}$=Leu $X_{21}$=Trp With 2 disulfide bridges between the cysteines 1-15 and 3-11.

EXAMPLE 12

Cys-Ser-Cys-Asn-Ser-Trp-Leu-Asp-Lys-Glu-Cys-Val-Tyr-Phe-Cys-His-Asp-Asp-Ile-Ile-Trp (SEQ ID NO: 21) (derivative of formula (I) ($X_1$=Cys $X_3$=Cys $X_4$=Asn $X_6$=Trp $X_9$=Lys $X_{11}$=Cys $X_{14}$=Phe $X_{17}$=Leu $X_{21}$=Trp With 2 disulfide bridges between the cysteines 1-15 and 3-11.

EXAMPLE 13

Cys-Ser-Ala-Phe-Ser-Ser-Leu-Asp-Lys-Glu-Ala-Val-Tyr-Phe-Cys-His-Leu-Asp-Ile-Ile-Trp (SEQ ID NO: 22) (derivative of formula (I) ($X_1$=Cys $X_3$=Ala $X_4$=Phe $X_6$=Ser $X_9$=Lys $X_{11}$=Ala $X_{14}$=Phe $X_{17}$=Leu $X_{21}$=Trp With 1 disulfide bridge between the cysteines 1 and 15.

EXAMPLE 14

Cys-Ser-Cys-Asn-Ser-Thr-Leu-Asp-Lys-Glu-Cys-Val-Tyr-Phe-Cys-His-Leu-Asp-Ile-Ile-Trp (SEQ ID NO:

23) (derivative of formula (I) ($X_1$=Cys $X_3$=Cys $X_4$=Asn $X_6$=Thr $X_9$=Lys $X_{11}$=Cys $X_{14}$=Phe $X_{17}$=Leu $X_{21}$=Trp With 2 disulfide bridges between the cysteines 1-15 and 3-11.

EXAMPLE 15

H-Ser-Cys-Phe-Ser-Ser-Leu-Asp-Lys-Glu-Ala-Val-Tyr-Phe-Cys-His-Leu-Asp-Ile-Ile-Trp (SEQ ID NO: 24) (derivative of formula (I) ($X_1$=H $X_3$=Cys $X_4$=Phe $X_6$=Ser $X_9$=Lys $X_{11}$=Ala $X_{14}$=Phe $X_{17}$=Leu $X_{21}$=Trp With a disulfide bridge between the cysteines 2 and 14.

EXAMPLE 16

H-Ser-Cys-Asn-Ser-Trp-Leu-Asp-Lys-Glu-Ala-Val-Tyr-Phe-Cys-His-Leu-Asp-Ile-Ile-Trp (SEQ ID NO: 25) (derivative of formula (I) ($X_1$=H $X_3$=Cys $X_4$=Asn $X_6$=Trp $X_9$=Lys $X_{11}$=Ala $X_{14}$=Phe $X_{21}$=Leu $X_{21}$=Trp With 1 disulfide bridge between the cysteines 2 and 14.

EXAMPLE 17

Cys-Ser-Ala-Asn-Ser-Trp-Leu-Asp-Lys-Glu-Ala-Val-Tyr-Phe-Cys-His-Leu-Asp-Ile-Ile-Trp (SEQ ID NO: 26) (derivative of formula (I) ($X_1$=Cys $X_3$=Ala $X_4$=Asn $X_6$=Trp $X_9$=Lys $X_{11}$=Ala $X_{14}$=Phe $X_{17}$=Leu $X_{21}$=Trp With a disulfide bridge between the cysteines 1-15. Each product was sequenced and its mass was verified by mass spectrometry.

EXAMPLE 18

An injectable solution corresponding to the following formulation was prepared:
Product of Example 1 1 mg
sterile aqueous excipient 2 ml

EXAMPLE 19

Tablets corresponding to the following formula were prepared:
Product of Example 1 2 mg
excipient q.s. one finished tablet weighing 150 mg (composition of the excipient: lactose, starch, talc, magnesium stearate).

STUDY OF THE ACTIVITY WITH RESPECT TO ENDOTHELIN RECEPTOR

A membrane preparation was made from rat posterior cortex plus cerebellum and the tissue was ground using a POLYTRON in 50 mM Tris buffer pH 7.4. After 30 minutes at 25° C. (water bath), the homogenate was centrifuged at 30,000 g for 15 minutes (2 centrifugations interspersed by taking up in Tris buffer pH 7.4).

The pellets were resuspended in an incubation buffer (25 mM Tris, pepstatin A 5 µg/ml, aprotinin 3 µg/ml, 0.1 mM PMSF, 3 mM EDTA, 1 mM EGTA pH 7.4).

2 ml aliquots were distributed in haemolysis tubes and [125I]endothelin (approximately 50,000 dpm/tube) and the test product were added. The product was first tested at $3 \times 10^5$M in triplicate. When the test product displaced by more than 50% the radioactivity specifically bound to the receptor, it was tested again in a series of 7 concentrations to determine the concentration which inhibited by 50% the radioactivity specifically bound to the receptor. The 50% inhibitory concentration was thereby determined.

Non-specific binding was determined by adding $10^{-6}$ M endothelin (in triplicate). The preparation was incubated at 25° C. for 60 minutes, put back on a water bath at 0° C. for 5 minutes, filtered off under reduced pressure and rinsed with 5 Tris buffer pH 7.4, and the radioactivity was counted in the presence of Triton scintillant. The result was expressed directly as a 50% inhibitory concentration ($IC_{50}$), that is to say as a concentration of test product, expressed in nM, required to displace 50% of the specific radioactivity bound to the receptor under study.

Result:

The $IC_{50}$ values found for the products of Examples 1 to 17 are given in Table I below, in nanomoles.

TABLE I

| EXAMPLE | $IC_{50}$ (nM) |
|---|---|
| 2 | 938 |
| 3 | 2.6 |
| 4 | 3.0 |
| 5 | 1.2 |
| 6 | 2.9 |
| 7 | 0.9 |
| 8 | 0.9 |
| 9 | 2.4 |
| 10 | 1.8 |
| 11 | 1.0 |
| 12 | 6.8 |
| 13 | 1.4 |
| 14 | 2.2 |
| 15 | 17 |
| 16 | 7.2 |
| 17 | 1.9 |

STUDY OF THE VASOCONSTRICTOR ACTIVITY AND ANTAGONISTIC ACTIVITY WITH RESPECT TO THE EFFECTS OF ENDOTHELIN IN PITHED RATS

Male Sprague-Dawley rats were anaesthetized with nembutal (60 mg/kg) injected intraperitoneally. The animals were then pithed and placed under assisted ventilation (1 ml/100 g—50 insufflations per minute), and thereafter the vagus nerves were sectioned. A carotid artery was catheterised to record arterial blood pressure and the test products were injected into the pudendal vein.

Study of the vasoconstrictor activity

The animals received endothelin 1 or the test compound intravenously in cumulative injections, the administration being at 2-minute intervals. The increase in arterial blood pressure (mABP) induced by each compound was measured expressed as a percentage change relative to the initial pressure.

Study of the endothelin-antagonist activity

Ten minutes after intravenous injection of the solvent or of the test compounds, the animals received administrations of endothelin 1 cumulatively (1, 3, 10 and 30 µg/kg i.v.) every 2 minutes. The antagonist activity was expressed as a percentage inhibition of the pressor response to endothelin administered alone at doses of 3 and 10 µg/kg.

Results:

The vasoconstrictor activity of the compound of Example 4 is given in Table II below:

The antagonist activity of the compound of Example 4 is given in Table III below:

TABLE III

| Example | Dose (μg/kg) | Percentage inhibition of responses to endothelin | |
|---|---|---|---|
| | | endothelin 3 μg | endothelin 10 μg |
| 4 | 1 | −43% | −45% |

Various modifications of the products and method of the invention may be made without departing from the spirit on scope thereof and it is to be understood that the invention is not intended to be limited only as defined in the appended claims.

TABLE II

| Example 4 | Dose (μg/kg) | % increase in mABP |
|---|---|---|
| 4 | 1 | +16% |

---

What is claimed is:

1. A peptide having the formula $$X_1-Ser-X_3-X_4-Ser-X_6-Leu-Asp-X_9-Glu-X_{11}- \\ \phantom{X_}1\phantom{-Ser-}3\phantom{-}4\phantom{-Ser-}6\phantom{-Leu-Asp-}9\phantom{-Glu-}11 \\ -Val-Tyr-X_{14}-Cys-His-X_{17}-Asp-Ile-Ile-X_{21} \text{ (SEQ ID NO: 1)} \\ \phantom{-Val-Tyr-}14\phantom{-Cys-His-}17\phantom{-Asp-Ile-Ile-}21$$

wherein
$X_3$ is hydrogen or cysteine residue,
$X_4$ is a cysteine or alanine residue,
$X_4$ is a residue selected from the group consisting of asparagine, phenylalanine, and glycine in the D series,
$X_6$ is a residue selected from the group consisting of tryptophan, serine, lysine, aspartic acid, tyrosine, and threonine in the D series,
$X_9$ and $X_{17}$ are a residue selected from the group consisting of glutamic acid, aspartic acid, lysine and leucine in the D series,
$X_{11}$ is a cysteine or alanine residue,
$X_{14}$ is a residue of tyrosine or phenylalanine in the D series,
$X_{21}$ is hydrogen or a tryptophan or D-tryptophan residue, and the derivatives possessing, where appropriate, one or two disulfide bridges, with the proviso that $X_{21}$ cannot be a tryptophan residue when $X_1$, $X_3$ and $X_{11}$ are a cysteine residue, $X_4$ is an asparagine residue, $X_6$ is a tryptophan residue, $X_9$ is a lysine residue, $X_{14}$ is a phenylalanine residue and $X_{17}$ is a leucine residue.

2. A peptide derivative of claim 1, wherein
$X_4$ is a residue of asparagine, phenylalanine, glycine in the D series,
$X_6$ is a residue of tryptophan, serine, lysine, aspartic acid, tyrosine, threonine in the D series,
$X_9$ and $X_{17}$ are a residue of glutamic acid, aspartic acid, lysine, leucine in the D series,
$X_{14}$ is a residue of tyrosine, phenylalanine in the D series,
$X_1$, $X_3$, $X_{11}$ and $X_{21}$ have the meaning of claim 1, and the derivatives possessing optionally one or two disulfide bridges.

3. A peptide of claim 1, wherein
$X_1$ is a cysteine residue,
$X_3$ is a cysteine or alanine residue,
$X_4$ is a residue of asparagine, phenylalanine, glycine in the D series,
$X_6$ is a residue of tryptophan, serine, lysine, aspartic acid, tyrosine, threonine in the D series,
$X_9$ and $X_{17}$ are a residue of glutamic acid, aspartic acid, lysine, leucine in the D series,
$X_{11}$ is a cysteine residue,
$X_{14}$ is a residue of tyrosine, phenylalanine in the D series,
$X_2$ is a residue of tryptophan in the D series, possessing optionally one or two disulfide bridges.

4. A peptide claim 3, selected from the group consisting of:
SEQ ID NO: 3,
SEQ ID NO: 4,
SEQ ID NO: 5,
SEQ ID NO: 6,
SEQ ID NO: 7,
SEQ ID NO: 8,
possessing optionally one or two disulfide bridges.

5. A peptide of claim 1, which is:
SEQ ID NO: 9,
and its derivatives possessing one or two disulfide bridges.

6. A composition of treating hypertension without vasoconstricting activity comprising an antihypertensively effective amount of a peptide of claim 5 and an inert pharmaceutical carrier.

7. A method of treating hypertension without vasoconstricting activity in warm-blooded animals comprising administering to warm-blooded animals in need thereof an antihypertensively effective amount of a peptide of claim 5.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i x ) FEATURE:
        ( D ) OTHER INFORMATION: Xaa at position 1 is a
            Cys or Ala residue. Xaa at position 4 is a
            residue of Asn, Phe, Leu, Ile, Ala, Val, Gly
            and their homologues in the D series. Xaa at
            position 6 is a residue of Trp, Phe, Leu,
            Ile, Ala, Val, Gly, Ser, Lys, Asp, Tyr, Thr
            and their homologues in the D series. Xaa at
            positions 9 and 17 are residues of Glu, Asp,
            Lys, Arg, Tyr, Leu and their homologues in
            the D series. Xaa at position 11 is a
            residue of Cys or Ala, Xaa at position 14 is
            a residue of Tyr, Phe, Leu, Ile, Ala, Val,
            Gly, Ser, Lys, Asp, Thr and their homologues
            in the D series, Xaa at position 21 is
            hydrogen or a residue of Trp or D-Trp ( x i ) SEQUENCE DESCRIPTION: SEQ ID NO:1:

```
Xaa  Ser  Xaa  Xaa  Ser  Xaa  Leu  Asp  Xaa  Glu  Xaa  Val  Tyr  Xaa  Cys
                       5                           10                          15
His  Xaa  Asp  Ile  Ile  Xaa
                 20
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i x ) FEATURE:
        ( D ) OTHER INFORMATION: Two disulfide bridges
            exist in this peptide, one between Cys
            residues at positions 1 and 15 and the other
            between Cys residues at positions 3 and 11

( x i ) SEQUENCE DESCRIPTION: SEQ ID NO:2:

```
Cys  Ser  Cys  Asn  Ser  Trp  Leu  Asp  Lys  Glu  Cys  Val  Tyr  Phe  Cys
                       5                           10                          15
His  Leu  Asp  Ile  Ile  Trp
                 20
```

( 2 ) INFORMATION FOR SEQ ID NO:3:

( i ) SEQUENCE CHARACTERISTICS:
    ( A ) LENGTH: 21 amino acids
    ( B ) TYPE: amino acid
    ( C ) STRANDEDNESS: unknown
    ( D ) TOPOLOGY: unknown ( x i ) SEQUENCE DESCRIPTION: SEQ ID NO:3:

```
Cys Ser Cys Phe Ser Ser Leu Asp Lys Glu Cys Val Tyr Phe Cys
              5                   10                  15
His Leu Asp Ile Ile Trp
         20
```

( 2 ) INFORMATION FOR SEQ ID NO:4:

( i ) SEQUENCE CHARACTERISTICS:
    ( A ) LENGTH: 21 amino acids
    ( B ) TYPE: amino acid
    ( C ) STRANDEDNESS: unknown
    ( D ) TOPOLOGY: unknown ( x i ) SEQUENCE DESCRIPTION: SEQ ID NO:4:

```
Cys Ser Cys Gly Ser Trp Leu Asp Lys Glu Cys Val Tyr Phe Cys
              5                   10                  15
His Leu Asp Ile Ile Trp
         20
```

( 2 ) INFORMATION FOR SEQ ID NO:5:

( i ) SEQUENCE CHARACTERISTICS:
    ( A ) LENGTH: 21 amino acids
    ( B ) TYPE: amino acid
    ( C ) STRANDEDNESS: unknown
    ( D ) TOPOLOGY: unknown ( x i ) SEQUENCE DESCRIPTION: SEQ ID NO:5:

```
Cys Ser Cys Asn Ser Ser Leu Asp Lys Glu Cys Val Tyr Phe Cys
              5                   10                  15
His Leu Asp Ile Ile Trp
         20
```

( 2 ) INFORMATION FOR SEQ ID NO:6:

( i ) SEQUENCE CHARACTERISTICS:
    ( A ) LENGTH: 21 amino acids
    ( B ) TYPE: amino acid
    ( C ) STRANDEDNESS: unknown
    ( D ) TOPOLOGY: unknown ( x i ) SEQUENCE DESCRIPTION: SEQ ID NO:6:

```
Cys Ser Cys Phe Ser Thr Leu Asp Lys Glu Cys Val Tyr Tyr Cys
              5                   10                  15
His Leu Asp Ile Ile Trp
         20
```

( 2 ) INFORMATION FOR SEQ ID NO:7:

( i ) SEQUENCE CHARACTERISTICS:
    ( A ) LENGTH: 21 amino acids
    ( B ) TYPE: amino acid
    ( C ) STRANDEDNESS: unknown
    ( D ) TOPOLOGY: unknown ( x i ) SEQUENCE DESCRIPTION: SEQ ID NO:7:

```
Cys Ser Cys Asn Ser Tyr Leu Asp Lys Glu Cys Val Tyr Phe Cys
              5                   10                  15
His Leu Asp Ile Ile Trp
         20
```

( 2 ) INFORMATION FOR SEQ ID NO:8:

( i ) SEQUENCE CHARACTERISTICS:
    ( A ) LENGTH: 21 amino acids
    ( B ) TYPE: amino acid
    ( C ) STRANDEDNESS: unknown
    ( D ) TOPOLOGY: unknown ( x i ) SEQUENCE DESCRIPTION: SEQ ID NO:8:

```
Cys Ser Cys Phe Ser Lys Leu Asp Lys Glu Cys Val Tyr Phe Cys
              5                   10                  15
His Leu Asp Ile Ile Trp
         20
```

( 2 ) INFORMATION FOR SEQ ID NO:9:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:9:
```
Cys Ser Cys Phe Ser Ser Leu Asp Lys Glu Cys Val Tyr Phe Cys
                 5                   10                   15
His Leu Asp Ile Ile Trp
                 20
```

( 2 ) INFORMATION FOR SEQ ID NO:10:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i x ) FEATURE:
        ( D ) OTHER INFORMATION: Xaa at position 21 is a
        hydrogen, two disulfide bridges exist, one
        between the Cys residues at positions 1 and
        15 and the other between the Cys residues at
        position 3 and 11

( x i ) SEQUENCE DESCRIPTION: SEQ ID NO:10:
```
Cys Ser Cys Asn Ser Ser Leu Asp Lys Glu Cys Val Tyr Phe Cys
                 5                   10                   15
His Leu Asp Ile Ile Xaa
                 20
```

( 2 ) INFORMATION FOR SEQ ID NO:11:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i x ) FEATURE:
        ( D ) OTHER INFORMATION: Xaa at position 21 is a
        hydrogen, two disulfide bridges exist, one
        between the Cys residues at positions 1 and
        15 and the other between Cys residues at
        positions 3 and 11

( x i ) SEQUENCE DESCRIPTION: SEQ ID NO:11:
```
Cys Ser Cys Asn Ser Trp Leu Asp Lys Glu Cys Val Tyr Phe Cys
                 5                   10                   15
His Leu Asp Ile Ile Xaa
                 20
```

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i x ) FEATURE:
        ( D ) OTHER INFORMATION: two disulfide bridges
        exist, one between Cys residues at positions
        1 and 15 and the other between Cys residues
        at positions 3 and 11

( x i ) SEQUENCE DESCRIPTION: SEQ ID NO:12:
```
Cys Ser Cys Phe Ser Trp Leu Asp Lys Glu Cys Val Tyr Phe Cys
                 5                   10                   15
His Leu Asp Ile Ile Trp
                 20
```

( 2 ) INFORMATION FOR SEQ ID NO:13:

( i ) SEQUENCE CHARACTERISTICS:
        ( A ) LENGTH: 21 amino acids
        ( B ) TYPE: amino acid

```
            ( C ) STRANDEDNESS: unknown
            ( D ) TOPOLOGY: unknown ( i x ) FEATURE:
            ( D ) OTHER INFORMATION: two disulfide bridges
                  exist, one between Cys residues at positions
                  1 and 15 and the other between Cys residues
                  at positions 3 and 11

( x i ) SEQUENCE DESCRIPTION: SEQ ID NO:13:
            Cys  Ser  Cys  Phe  Ser  Ser  Leu  Asp  Lys  Glu  Cys  Val  Tyr  Phe  Cys
                           5                           10                          15
            His  Leu  Asp  Ile  Ile  Trp
                           20
```

( 2 ) INFORMATION FOR SEQ ID NO:14:

```
    ( i ) SEQUENCE CHARACTERISTICS:
            ( A ) LENGTH: 21 amino acids
            ( B ) TYPE: amino acid
            ( C ) STRANDEDNESS: unknown
            ( D ) TOPOLOGY: unknown ( i x ) FEATURE:
            ( D ) OTHER INFORMATION: two disulfide bridges
                  exist, one between Cys residues at positions
                  1 and 15 and the other between Cys residues
                  at positions 3 and 11

( x i ) SEQUENCE DESCRIPTION: SEQ ID NO:14:
            Cys  Ser  Cys  Asn  Ser  Tyr  Leu  Asp  Lys  Glu  Cys  Val  Tyr  Phe  Cys
                           5                           10                          15
            His  Leu  Asp  Ile  Ile  Trp
                           20
```

( 2 ) INFORMATION FOR SEQ ID NO:15:

```
    ( i ) SEQUENCE CHARACTERISTICS:
            ( A ) LENGTH: 21 amino acids
            ( B ) TYPE: amino acid
            ( C ) STRANDEDNESS: unknown
            ( D ) TOPOLOGY: unknown ( i x ) FEATURE:
            ( D ) OTHER INFORMATION: two disulfide bridges
                  exist, one between Cys residues at positions
                  1 and 15 and the other between Cys residues
                  at positions 3 and 11

( x i ) SEQUENCE DESCRIPTION: SEQ ID NO:15:
            Cys  Ser  Cys  Phe  Ser  Ser  Leu  Asp  Glu  Glu  Cys  Val  Tyr  Phe  Cys
                           5                           10                          15
            His  Leu  Asp  Ile  Ile  Trp
                           20
```

( 2 ) INFORMATION FOR SEQ ID NO:16:

```
    ( i ) SEQUENCE CHARACTERISTICS:
            ( A ) LENGTH: 21 amino acids
            ( B ) TYPE: amino acid
            ( C ) STRANDEDNESS: unknown
            ( D ) TOPOLOGY: unknown ( i x ) FEATURE:
            ( D ) OTHER INFORMATION: two disulfide bridges
                  exist, one between Cys residues at positions
                  1 and 15 and the other between Cys residues
                  at positions 3 and 11

( x i ) SEQUENCE DESCRIPTION: SEQ ID NO:16:
            Cys  Ser  Cys  Gly  Ser  Trp  Leu  Asp  Lys  Glu  Cys  Val  Tyr  Phe  Cys
                           5                           10                          15
            His  Leu  Asp  Ile  Ile  Trp
                           20
```

( 2 ) INFORMATION FOR SEQ ID NO:17:

```
    ( i ) SEQUENCE CHARACTERISTICS:
            ( A ) LENGTH: 21 amino acids
            ( B ) TYPE: amino acid
            ( C ) STRANDEDNESS: unknown
            ( D ) TOPOLOGY: unknown
```

( i x ) FEATURE:
    ( D ) OTHER INFORMATION: two disulfide bridges
        exist, one between Cys residues at positions
        1 and 15 and the other between Cys residues
        at positions 3 and 11

( x i ) SEQUENCE DESCRIPTION: SEQ ID NO:17:

Cys Ser Cys Asn Ser Ser Leu Asp Lys Glu Cys Val Tyr Phe Cys
                    5                   10                  15
His Leu Asp Ile Ile Trp
                    20

( 2 ) INFORMATION FOR SEQ ID NO:18:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i x ) FEATURE:
        ( D ) OTHER INFORMATION: two disulfide bridges
            exist, one between Cys residues at positions
            1 and 15 and the other between Cys residues
            at positions 3 and 11

( x i ) SEQUENCE DESCRIPTION: SEQ ID NO:18:

Cys Ser Cys Phe Ser Asp Leu Asp Lys Glu Cys Val Tyr Phe Cys
                    5                   10                  15
His Leu Asp Ile Ile Trp
                    20

( 2 ) INFORMATION FOR SEQ ID NO:19:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i x ) FEATURE:
        ( D ) OTHER INFORMATION: two disulfide bridges
            exist, one between Cys residues at positions
            1 and 15 and the other between Cys residues
            at positions 3 and 11

( x i ) SEQUENCE DESCRIPTION: SEQ ID NO:19:

Cys Ser Cys Phe Ser Lys Leu Asp Lys Glu Cys Val Tyr Phe Cys
                    5                   10                  15
His Leu Asp Ile Ile Trp
                    20

( 2 ) INFORMATION FOR SEQ ID NO:20:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i x ) FEATURE:
        ( D ) OTHER INFORMATION: two disulfide bridges
            exist, one between Cys residues at positions
            1 and 15 and the other between Cys residues
            at positions 3 and 11

( x i ) SEQUENCE DESCRIPTION: SEQ ID NO:20:

Cys Ser Cys Phe Ser Thr Leu Asp Lys Glu Cys Val Tyr Tyr Cys
                    5                   10                  15
His Leu Asp Ile Ile Trp
                    20

( 2 ) INFORMATION FOR SEQ ID NO:21:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i x ) FEATURE:

(D) OTHER INFORMATION: two disulfide bridges
exist, one between Cys residues at positions
1 and 15 and the other between Cys residues
at positions 3 and 11

(x i) SEQUENCE DESCRIPTION: SEQ ID NO:21:

Cys Ser Cys Asn Ser Trp Leu Asp Lys Glu Cys Val Tyr Phe Cys
                  5                   10                  15
His Asp Asp Ile Ile Trp
              20

(2) INFORMATION FOR SEQ ID NO:22:

(i) SEQUENCE CHARACTERISTICS:
    (A) LENGTH: 21 amino acids
    (B) TYPE: amino acid
    (C) STRANDEDNESS: unknown
    (D) TOPOLOGY: unknown (ix) FEATURE:
    (D) OTHER INFORMATION: one disulfide bridge
        exists between Cys residues at positions 1
        and 15

(x i) SEQUENCE DESCRIPTION: SEQ ID NO:22:

Cys Ser Ala Phe Ser Ser Leu Asp Lys Glu Ala Val Tyr Phe Cys
                  5                   10                  15
His Leu Asp Ile Ile Trp
              20

(2) INFORMATION FOR SEQ ID NO:23:

(i) SEQUENCE CHARACTERISTICS:
    (A) LENGTH: 21 amino acids
    (B) TYPE: amino acid
    (C) STRANDEDNESS: unknown
    (D) TOPOLOGY: unknown (ix) FEATURE:
    (D) OTHER INFORMATION: two disulfide bridges
        exist, one between Cys residues at positions
        1 and 15 and the other between Cys residues
        at positions 3 and 11

(x i) SEQUENCE DESCRIPTION: SEQ ID NO:23:

Cys Ser Cys Asn Ser Thr Leu Asp Lys Glu Cys Val Tyr Phe Cys
                  5                   10                  15
His Leu Asp Ile Ile Trp
              20

(2) INFORMATION FOR SEQ ID NO:24:

(i) SEQUENCE CHARACTERISTICS:
    (A) LENGTH: 21 amino acids
    (B) TYPE: amino acid
    (C) STRANDEDNESS: unknown
    (D) TOPOLOGY: unknown (ix) FEATURE:
    (D) OTHER INFORMATION: Xaa at position 1 is
        a hydrogen, one disulfide bridge exists
        between Cys residues at positions 3 and 15

(x i) SEQUENCE DESCRIPTION: SEQ ID NO:24:

Xaa Ser Cys Phe Ser Ser Leu Asp Lys Glu Ala Val Tyr Phe Cys
                  5                   10                  15
His Leu Asp Ile Ile Trp
              20

(2) INFORMATION FOR SEQ ID NO:25:

(i) SEQUENCE CHARACTERISTICS:
    (A) LENGTH: 21 amino acids
    (B) TYPE: amino acid
    (C) STRANDEDNESS: unknown
    (D) TOPOLOGY: unknown (ix) FEATURE:
    (D) OTHER INFORMATION: Xaa at position 1 is
        a hydrogen, a disulfide bridge exists
        between Cys residues at positions 3 and 15

(xi) SEQUENCE DESCRIPTION: SEQ ID NO:25:

Xaa Ser Cys Asn Ser Trp Leu Asp Lys Glu Ala Val Tyr Phe Cys
                5                          10                         15
His Leu Asp Ile Ile Trp
            20

(2) INFORMATION FOR SEQ ID NO:26:

(i) SEQUENCE CHARACTERISTICS:
  (A) LENGTH: 21 amino acids
  (B) TYPE: amino acid
  (C) STRANDEDNESS: unknown
  (D) TOPOLOGY: unknown (ix) FEATURE:
  (D) OTHER INFORMATION: A disulfide bridge exists between Cys residues at positions 3 and 15

(xi) SEQUENCE DESCRIPTION: SEQ ID NO:26:

Cys Ser Ala Asn Ser Trp Leu Asp Lys Glu Ala Val Tyr Phe Cys
                5                          10                         15
His Leu Asp Ile Ile Trp
            20